United States Patent [19]
Bergström et al.

[11] Patent Number: 5,685,713
[45] Date of Patent: Nov. 11, 1997

[54] DEPTH GAUGE AND METHOD OF TREATING A DEPTH GAUGE

[75] Inventors: Nils Gustaf Bergström, Vagnhärad; Leif Broberg, Göteborg; Anders Holmén, Billdal, all of Sweden

[73] Assignee: Astra Aktiebolag, Sodertalje, Sweden

[21] Appl. No.: 424,415

[22] PCT Filed: Oct. 25, 1993

[86] PCT No.: PCT/SE93/00870

§ 371 Date: Apr. 26, 1995

§ 102(e) Date: Apr. 26, 1995

[87] PCT Pub. No.: WO94/09719

PCT Pub. Date: May 11, 1994

[30] Foreign Application Priority Data

Oct. 28, 1992 [SE] Sweden ............... 9203183

[51] Int. Cl.⁶ .................. A61C 19/04; A61C 8/00
[52] U.S. Cl. ............................ 433/72; 433/141
[58] Field of Search .................. 433/30, 141, 143, 433/75, 72; 33/513, 514

[56] References Cited

U.S. PATENT DOCUMENTS

| | | | |
|---|---|---|---|
| 4,289,848 | 9/1981 | Miller et al. | 433/72 |
| 4,364,730 | 12/1982 | Axelsson | 433/141 |
| 4,552,531 | 11/1985 | Martin | 433/141 |
| 4,768,952 | 9/1988 | Loewenthal | 433/72 |
| 5,044,951 | 9/1991 | Sheridan | 433/72 |
| 5,125,838 | 6/1992 | Seigneurin | 433/102 |
| 5,137,447 | 8/1992 | Hunter | 433/72 |
| 5,178,537 | 1/1993 | Currie | 433/72 |
| 5,193,999 | 3/1993 | Staubli | 433/72 |
| 5,271,734 | 12/1993 | Takeuchi | 433/72 |
| 5,318,442 | 6/1994 | Jeffcoat et al. | 433/72 |

FOREIGN PATENT DOCUMENTS

| | | |
|---|---|---|
| 0119813 | 9/1984 | European Pat. Off. |
| 290446 | 8/1953 | Switzerland |

*Primary Examiner*—Paul J. Hirsch
*Attorney, Agent, or Firm*—White & Case

[57] ABSTRACT

The present invention relates to a device for determining the correct lengths of standardized components of a dental implant system in situ in the oral cavity. The device comprises an elongate gauge body (1, 2) being provided with circumferential dark bands (10, 18, 19, 20, 21) located at predetermined distances from each other and having predetermined widths, the areas between said darker bands having a pronouncedly lighter colour, each boundary line between lighter and darker bands corresponding to one specific, standardized component.

7 Claims, 2 Drawing Sheets

DEPTH GAUGE AND METHOD OF TREATING A DEPTH GAUGE

TECHNICAL FIELD OF THE INVENTION

The present invention relates to a device for determining the correct lengths in situ of standardized components of a dental implant system to be used in the oral cavity, more particularly to a device for measuring the depth of holes drilled or bored into the jaw bone for the subsequent insertion of fixtures for dental prostheses as well as to a device for facilitating the correct choice of an abutment for bridging the soft tissue around the hole and to be mounted on a fixture inserted into said hole. The invention also relates to a method for treating said device.

BACKGROUND TO THE INVENTION

A system for dental prostheses commonly used today comprises a more or less cylindrical fixture which is inserted into a bore-hole drilled into the uncovered jawbone. The system further comprises a conical abutment or pillar, intended to carry the prosthesis, which is to be attached to the fixture, thus bridging the layer of soft tissue covering the jawbone. The abutment is complementary to a conical bore in the top of the fixture. The abutment is provided in several standard lengths in order to allow the correct choice of abutment in dependence of the thickness of the soft tissue around the implant site after implantation.

The choice of the correct abutment is very important inter alia for aesthetic reasons. This choice may however be time-consuming and may also be troublesome for the patient. There thus is a need for a tool which facilitates the choice of abutment and which is simple to use and to read in the environment of the oral cavity.

It may also be difficult to chose the correct fixture which is to fit into the hole drilled into the bone. It is important that the fixture is flush with the uncovered bone tissue or slightly below the edge of the bore-hole.

Generally, when implants are fitted into bone tissue, different kinds of metallic surgical tools are used to prepare the site in the tissue where the implant is to be located. These tools normally are made of carbon steel (normally in disposable tools) or surgical grade stainless steel or titanium or titanium alloys (normally in non-disposable tools).

In some cases it may be advantageous if at least the surface of the tools are covered with a material which is more biocompatible than the material in the tool even if the tool is not to remain in the bone tissue for a long period of time.

If the tool is not of an inert material as regards the chemical environment prevalent in bone tissue and blood, some slight contaminations may affect the sides of the bore hole. These contaminants might possibly affect the so-called osseointegration process which seems to be very important in connection with bone implants and which seems to be sensitive in respect of contaminants.

Another prerequisite for a good osseointegration is a good, stable fit between bone tissue and implants, the osseointegration being dependent on a close contact between bone tissue and implant surface. When a bore-hole for an implant has been drilled, it therefore is important that the length of the bore-hole corresponds as closely as possible to the length of the implant chosen.

If the bore-hole in the jaw-bone should happen to be to shallow for the implant which has been deemed to be suitable in a specific location in the oral cavity, it is important to be able to ascertain this in advance, because of the trauma to the bone tissue that might be the consequence of the implant first being screwed into the bore-hole and then being unscrewed again. If it is vital that the implant chosen actually is used in this specific location, the threads in the bore also might be damaged by the necessary, additional drilling procedure.

BRIEF DESCRIPTION OF THE INVENTION CONCEPT

The above object is achieved in that said device comprises an elongate body being provided with circumferential dark bands located at pre-determined distances from each other and having pre-determined widths, the areas between said darker bands having a pronouncedly lighter colour, each boundary line between lighter and darker bands corresponding to one specific, standardized component.

In a preferred embodiment said darker bands have been etched, by means of a laser beam, in a layer of brightly coloured titanium nitride covering the surface of the device, or, in case the device is made by titanium or titanium alloy, the bands may be etched directly in the titanium surface.

Further advantageous embodiments of the invention are set forth in the dependent claims.

BRIEF DESCRIPTION OF THE APPENDED DRAWINGS

FIG. 1 illustrates one side of preferred embodiment of a combined device in accordance with the invention, FIG. 2 shows the other side of the device in FIG. 1, FIG. 3 illustrates a preferred embodiment of the device for determining the length of an abutment to be used, FIG. 4 shows the preferred embodiment of a device for determining the depth of a bore-hole in the jaw-bone, FIG. 5 a detail of the device in FIG. 4.

DETAILED DESCRIPTION OF A PREFERRED EMBODIMENT OF THE INVENTION

Figure 1:
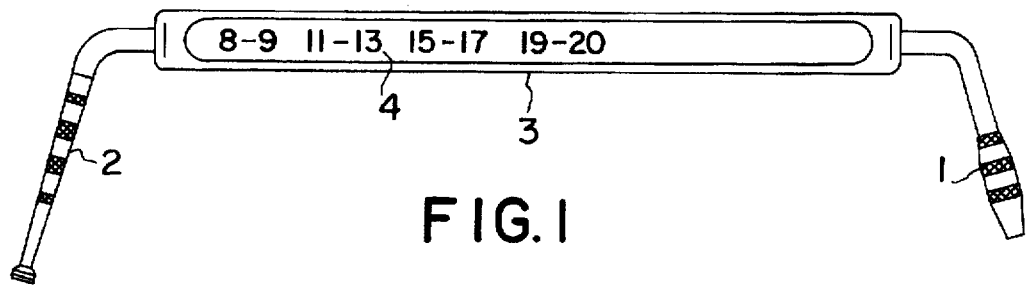
Figure 2:
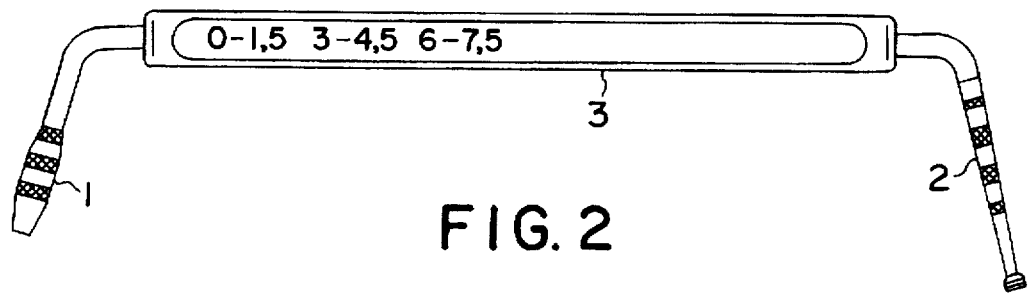

As can be seen in FIGS. 1 and 2, a preferred embodiment of the invention comprises a body 1 or abutment gauge for determining the correct length of an abutment, a body 2 or fixture gauge for determining the depth of a hole drilled into the jawbone and a handle 3 joining the two gauge bodies. The gauges are angled relative to the handle in order to facilitate the use of the tool or device in the oral cavity. FIG. 1 further illustrates that one side of the handle is provided with numerals 4 indicating the lengths of the different standard fixtures and FIG. 2 illustrates the markings on the other side of the handle corresponding to the different sizes of abutments.

Figure 3:
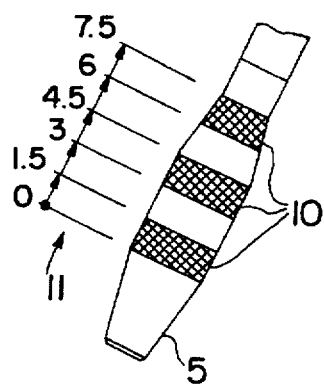
Figure 7:
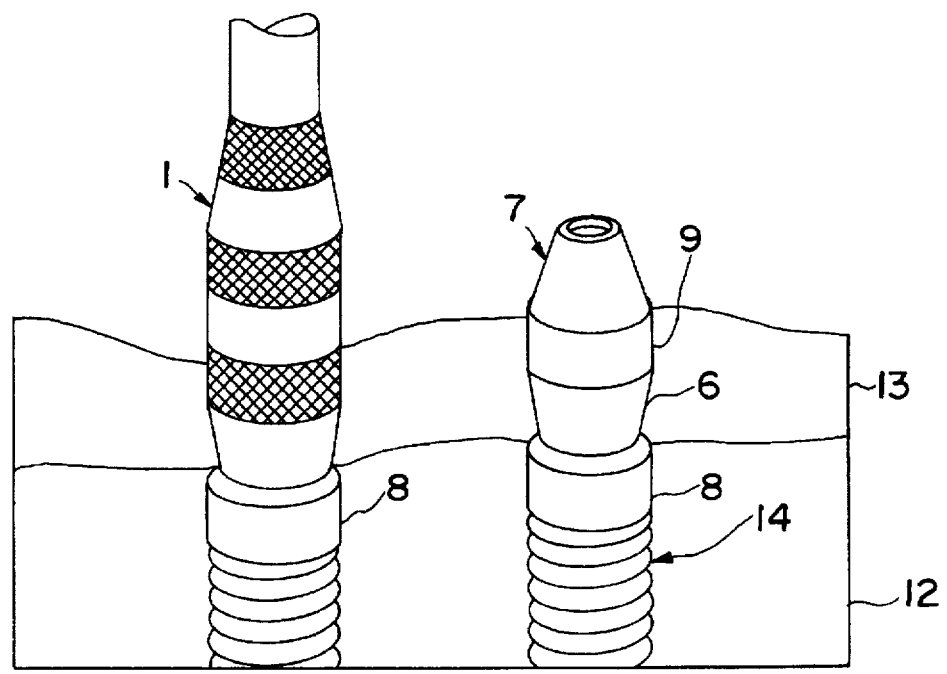

FIGS. 3 and 7 show the construction and use of the abutment gauge in more detail. As can be seen in FIG. 3, the lower part 5 of the abutment gauge has a conical or tapering shape which corresponds exactly to the shape of the lower part 6 of an abutment 7 (FIG. 7). The upper part of the abutment gauge is provided with circumferential dark bands 10. The bands 10 are spaced equidistantly over the body of the gauge. As indicated by the chain of measurements 11, the distance between the bands and the width of the bands in this particular case is 1.5 mm. Each boundary line will correspond to a specific length of the cylindrical part 9 of the abutments 7.

The free end of the lower part 5 may be provided with a relatively short, cylindrical projection having a rounded end which preferably is hemispherical. The cylindrical part of the projection is complementary to a cylindrical continuation of the conical bore in the fixture 8 and will by these means ensure a correct orientation of the lower part 5 when this part is inserted into the fixture. The rounded part of the projection will facilitate the insertion of the abutment gauge into the conical bore of the fixture.

As can be seen in FIG. 7, the conical part of the abutment gauge 1 is inserted in the fixture 8, which is located in a bore-hole in the bone tissue of the jaw-bone 12. The thickness of the soft tissue covering the jaw-bone 12 can be measured against an adjacent boundary line between a dark band and a light band, allowing the correct choice of an abutment for this particular fixture. The titanium nitride has a bright yellow colour and the darker bands are almost black, and consequently a very distinct level indication is given at each boundary line between darker bands and lighter areas. This level indication will be very easy to read in the conditions prevalent in the oral cavity regarding for instance light and available space. It should be noted that the contrast between the darker bands and the lighter bands on a titanium gauge also is sufficient to give the above, distinct level indication.

Figure 4:
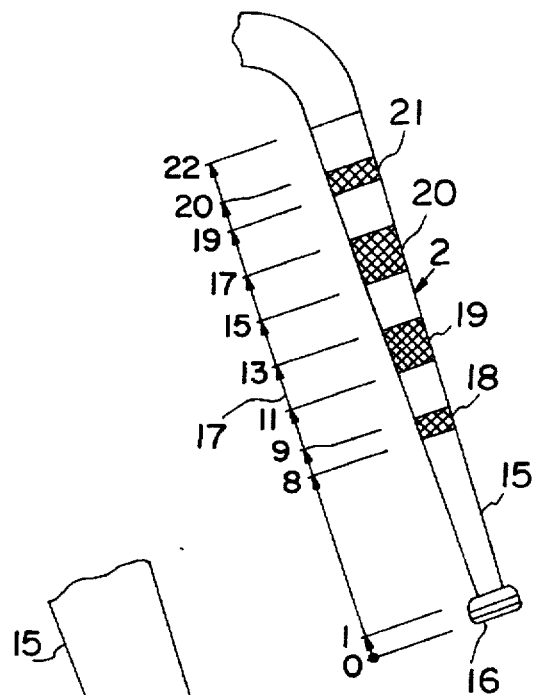
Figure 5:
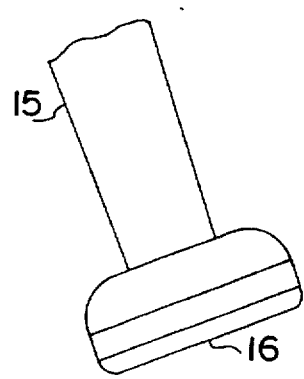
Figure 6:
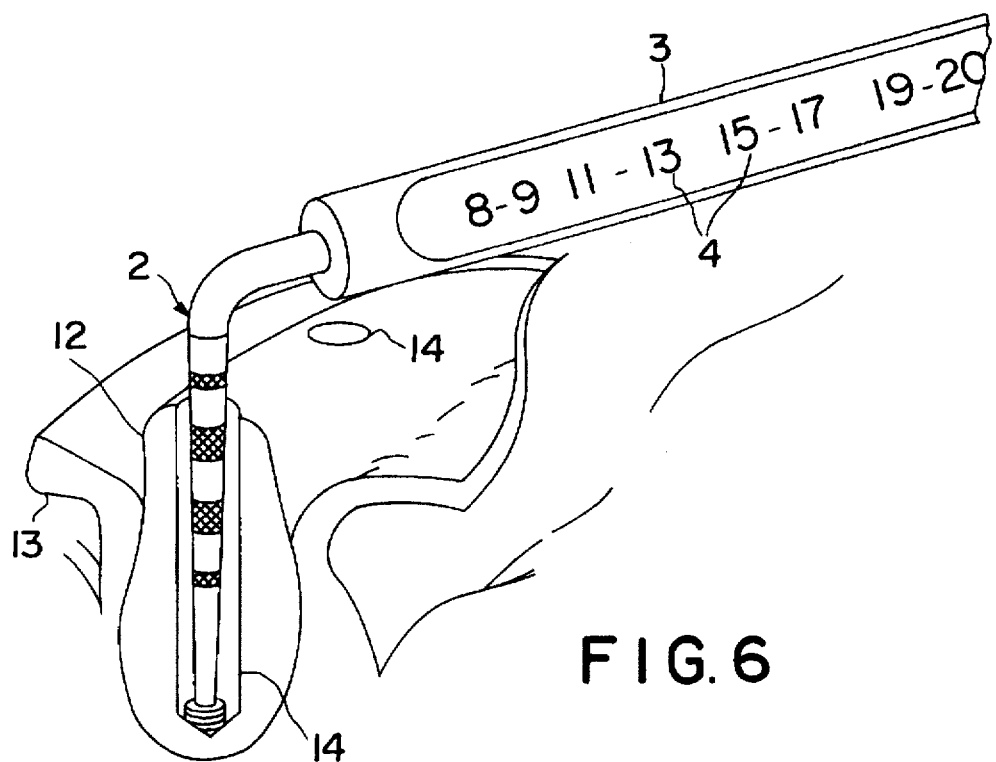

The details of the fixture gauge and its use are illustrated in FIGS. 4, 5 and 6. As indicated in FIG. 4, the fixture gauge comprises an elongate, conically tapering rod 15 which at its free end is provided with a transversely oriented plate or button 16 which is seen in more detail in FIG. 5.

As indicated by means of the chain of measurements 17, a dark band 18 having a width of 1 mm is located at a distance of 8 mm from the tip of the rod 2. Each following dark band 19, 20, 21 is separated from the adjacent band by means of a space having a width of exactly 2 mm. Again, a very distinct level indication is given at each boundary line between darker bands and lighter areas. The button 16 also has a defined thickness, in this case 1 mm.

The fixture gauge is inserted into an uncovered bore-hole 14 in the jaw-bone 12, the button 16 being slid along the side-wall of the hole until it reaches the corner formed by the side-wall and the bottom of the hole (the bottom of the hole normally being slightly conical due to the shape of the drills normally used) and the depth of the hole is read against the bands of the gauge, allowing the correct fixture to be chosen. If there should be any doubt whether the corner has been reached, this can be checked by moving the gauge to the middle of the hole. The difference in depth should not be more than maximally 0.4 mm with regard to the specific fixture diameters used in the above system.

The button is particularly important when holes in the upper jaw are measured. These holes may some times extend into the sinusoidal cavity, and in this case it is important to measure the thickness of the bone tissue. This may be done by hooking the button on the edge of the hole in the cavity and reading the thickness of the bone tissue at the edge of the hole in the oral cavity against the bands on the rod, taking into account that exactly 1 mm should be subtracted from the measurement obtained due to the thickness of the button.

Bone implants may also be relatively smooth instead of being provided with threads. This kind of implants may be carefully tapped into place in a borehole in the bone, which bore-hole may have a slightly narrower diameter than the implant, by means of a small hammer. However carefully this is done, there always is a risk that the fixture may be pushed to far down into the hole if the hole does not exactly correspond to the fixture. The fixture gauge according to the invention thus may be particularly useful in this case, since it may be difficult to extricate an implant which has been pushed to far down into a hole.

These problems might also arise if the bore-hole is to shallow for the implant since the act of extrication per se might cause a trauma to the walls of the bore-hole which might have a deleterious influence on the osseointegration process.

If the surface of the bone into which the fixture is to be inserted is obliquely oriented relative to the longitudinal direction of the hole, the above-mentioned boundarys on the fixture gauge will also serve as indexes on a ruler for measuring the difference in level between the edges of the bore-hole and will consequently be very useful when determining how deep the hole has to be in order to house the implant correctly in relation to the oblique surface of the bone.

The device according to the invention can be treated by the following steps:

a) coating the gauge with a thin layer of titanium nitride (TiN) by means of chemical vapour deposition until the drill obtains a bright permanent colour, b) etching circumferential bands with pre-determined widths being located at pre-determined distances from each other around the outer surface of the body by means of a laser beam, the bands thus being dark and sharply defined.

In case the gauge is made of titanium or titanium alloys, the darker bands may be laser-etched directly in the titanium surface. It is however also quite within the scope of the invention to cover a gauge made of titanium or an alloy thereof with TiN and etching the bands therein.

The use of a laser beam has the advantage that the boundary lines will be very sharp and well defined and that the contrast between darker and lighter areas will be high.

The etched areas will remain essentially smooth in spite of the treatment, which ensures that there will be no rough areas on the device upon which contaminants easily will adhere.

It should be emphasized that the invention is not limited to the embodiment described above and can be varied in many ways within the scope of the appended claims.

We claim:

1. A surgical instrument for use in the surgical procedure for implanting a dental implant system of the type which includes:

a fixture component part having a leading end and a trailing end and adapted to be anchored in a jaw bone of a patient by insertion of the leading end thereof into a bore which extends into the jaw bone from a surface thereof, the fixture component part being a standard fixture component part of predetermined length and selected from a set of standard fixture component parts of different predetermined lengths so that on anchorage of the fixture component part in the jaw bone the trailing end is essentially flush with the surface of the jaw bone; and an abutment component part for bridging a layer of soft tissue which covers the surface of the jaw bone to couple a dental prosthesis to the fixture component part, the abutment component part having a leading end which is adapted to be inserted through a surface of the soft tissue layer and to mate with the trailing end of the fixture component part in the jaw bone and a trailing end which when the leading end of the abutment component part mates with the trailing end of the fixture component part projects from the surface of the soft tissue layer and is adapted to support the dental prosthesis, the abutment component part being a standard abutment component part of predetermined length and selected from a set of standard abutment component parts of different predetermined lengths so that when the leading end of the abutment component part mates with the trailing end of the fixture component part essentially only the trailing end of the abutment component part which supports the dental prosthesis projects from the surface of the soft tissue layer;

wherein the surgical instrument comprises:

a depth gauge body having a leading end, a trailing end and an outer peripheral surface extending between the leading and trailing ends, wherein the leading end of the depth gauge body is a replica of the leading end of the abutment component part and adapted to be inserted through the surface of the soft tissue layer to mate with the trailing end of the fixture component part in the jaw bone, wherein the outer peripheral surface of the depth gauge body is provided with a series of alternate dark and light colored bands of predetermined widths, the boundary lines between adjacent dark and light colored bands representing standard abutment component parts of different predetermined length in the set thereof, and further wherein when the leading end of the depth gauge body mates with the trailing end of the fixture component part in the jaw bone the depth of the soft tissue layer is able to be determined from the boundary lines which project from the surface of the soft tissue layer whereby a standard abutment component part of correct predetermined length is able to be selected from the set of standard abutment component parts.

2. An instrument according to claim 1, wherein the leading end of the depth gauge body is presented by a leading portion of the outer peripheral surface, wherein the leading portion of the outer peripheral surface defines a shape which corresponds to the shape of that portion of the abutment component part which presents the leading end of the abutment component part and wherein the series of alternate dark and light colored bands is provided on the outer peripheral surface of the depth gauge body which extends between the leading portion and the trailing end.

3. An instrument according to claim 1, wherein the depth gauge body is a first depth gauge body, wherein the instrument presents a second depth gauge body having a leading end, a trailing end and an outer peripheral surface extending between the leading and trailing ends, wherein the leading end of the second depth gauge is adapted to be inserted into the bore in the jaw bone, wherein the outer peripheral surface of the second depth gauge body is provided with a series of alternate dark and light colored bands of predetermined widths, the boundary lines between adjacent dark and light colored bands on the second depth gauge body representing standard fixture component parts of different predetermined length in the set thereof, and further wherein insertion of the leading end of the second depth gauge into the bore in the jaw bone enables the depth of the bore to be determined from the boundary lines which project above the surface of the jaw bone whereby a standard fixture component part of correct predetermined length is able to be selected from the set of standard fixture components.

4. An instrument according to claim 3, wherein the leading end of the second depth gauge body defines a transversely oriented button or plate.

5. An instrument according to claim 3, wherein the outer peripheral surface of each depth gauge body is coated with a thin layer of titanium nitride (TiN) and wherein the bands of dark color are bands of laser etched titanium nitride.

6. An instrument according to claim 3, wherein the trailing ends of the first and second depth gauge bodies are connected to one another by a handle.

7. A method of manufacturing a surgical instrument according to claim 3, the method including the steps of:

(i) forming each depth gauge body from a metal selected from the group consisting of surgical grade stainless steel, surgical grade carbon steel, titanium and titanium alloys;

(ii) coating the outer peripheral surface of each depth gauge body with a thin layer of titanium nitride (TiN) by chemical vapor deposition until the outer peripheral surface of the depth gauge body obtains a permanent bright color; and (iii) etching the outer peripheral surface of each depth gauge body with a laser beam so as to produce a plurality of dark bands on the outer peripheral surface of the depth gauge body of predetermined widths and spacing.

* * * * *